(12) United States Patent
Pluschke et al.

(10) Patent No.: US 7,569,541 B2
(45) Date of Patent: Aug. 4, 2009

(54) METHOD FOR SYNTHESIZING CONFORMATIONALLY CONSTRAINED PEPTIDES, PEPTIDOMIMETICS AND THE USE THEREOF AS SYNTHETIC VACCINES

(75) Inventors: Gerd Pluschke, Bad Kronzing (DE); Ursula Kienzl, Zurich (CH); John Robinson, Wermatswil (CH); Rinaldo Zurbriggen, Schmitten (CH)

(73) Assignee: Mymetics Corporation, New York, NY (US)

( * ) Notice: Subject to any disclaimer, the term of this patent is extended or adjusted under 35 U.S.C. 154(b) by 122 days.

(21) Appl. No.: 10/559,010

(22) PCT Filed: Jun. 2, 2004

(86) PCT No.: PCT/EP2004/005952

§ 371 (c)(1),
(2), (4) Date: Mar. 20, 2006

(87) PCT Pub. No.: WO2004/106366

PCT Pub. Date: Dec. 9, 2004

(65) Prior Publication Data

US 2006/0258564 A1    Nov. 16, 2006

(30) Foreign Application Priority Data

Jun. 2, 2003  (DE)  ................... 03012520

(51) Int. Cl.
*A61K 38/12*  (2006.01)
(52) U.S. Cl. ......................... 514/11; 530/317
(58) Field of Classification Search .................. None
See application file for complete search history.

(56) References Cited

OTHER PUBLICATIONS

Zhang et al., "Novel Cyclic Analogs of Angiotensin II with Cyclization between Positions 5 and 7: Conformational and Biological Implications," J. Med. Chem., 1996, 39, 2738-44.*

Pfeiffer et al., "A Virosome-Mimotope Approach to Synthetic Vaccine Design and Optimization: Synthesis, Conformation, and Immune Recognition of a Potential Malaria-Vaccine Candidate," Angew Chem. Int. Ed., 2003, 42, 2368-71.*

Moreno et al., "Exploiting Conformationally Constrained Peptidomimetics and an Efficient Human-Compatible Delivery System in Synthetic Vaccine Design" ChemBioChem, 2001, 2, 838-43.*

Pfieffer et al. Applicatoin of Protein Epitope Memetis in Vaccine Design. A new Supersecondary Structure in the Circumsporozoite Protein of *Plasmodium falciparum*? Chimia, vol. 55, pp. 334-339. 2001.*

Bisang et al. "A Diketopiperazine-Based Template to Stabilize Loop Conformations in Cyclic Peptides Containing the NPNA and RGD Motifs." HELVETICCAH IMICAAC TA~vol. 79 (1996) pp. 1825-1842.*

Nardin, Elizabeth H., "The Use of Multiple Antigen Peptides in the Analysis and Induction of Protective Immune Responses against Infectious Diseases", Advances In Immunology, vol. 60, pp. 105-149, (1995).

Nussenzweig, Victor, "Rationale for the Development of an Engineered Sporozoite Malaria Vaccine", Advances in Immunology, vol. 45, pp. 283-334, (1989).

Togna, A. Rita, "Synthetic *Plasmodium falciparum* Circumsporozoite Peptides Elicit Heterogenous L3T4[+] T Cell Proliferative Responses in H-2$^b$ Mice", The Journal of Immunology, vol. 137, pp. 2956-2960, No. 9, (1986).

Zavala, Fidel, "Rationale for Development of a Synthetic Vaccine Against *Plasmodium falciparum* Malaria", Science, vol. 228, pp. 1436-1440, (1985).

* cited by examiner

*Primary Examiner*—Anish Gupta
(74) *Attorney, Agent, or Firm*—Proskauer Rose LLP

(57) ABSTRACT

The present invention relates to methods for synthesizing conformationally constrained peptides and cyclic peptidomimetics obtainable by these methods which are conformationally constrained due an internal cross-link. This cross-link is formed between the side chain of an amino acid residue or analog and a (2S, 4S)4-functionalized proline residue. The invention further relates to the use of (2S, 4S)-4-functionalized proline residues as building units in the synthesis of such peptidomimetics and to the use thereof as antigens, alone or in combination with suitable immunopotentiating delivery systems, for example immunopotentiating reconstituted influenza virosomes to elicit an immune response in a mammal. Moreover, the invention also relates to pharmaceutical compositions containing the same.

11 Claims, 3 Drawing Sheets

Figure 1:
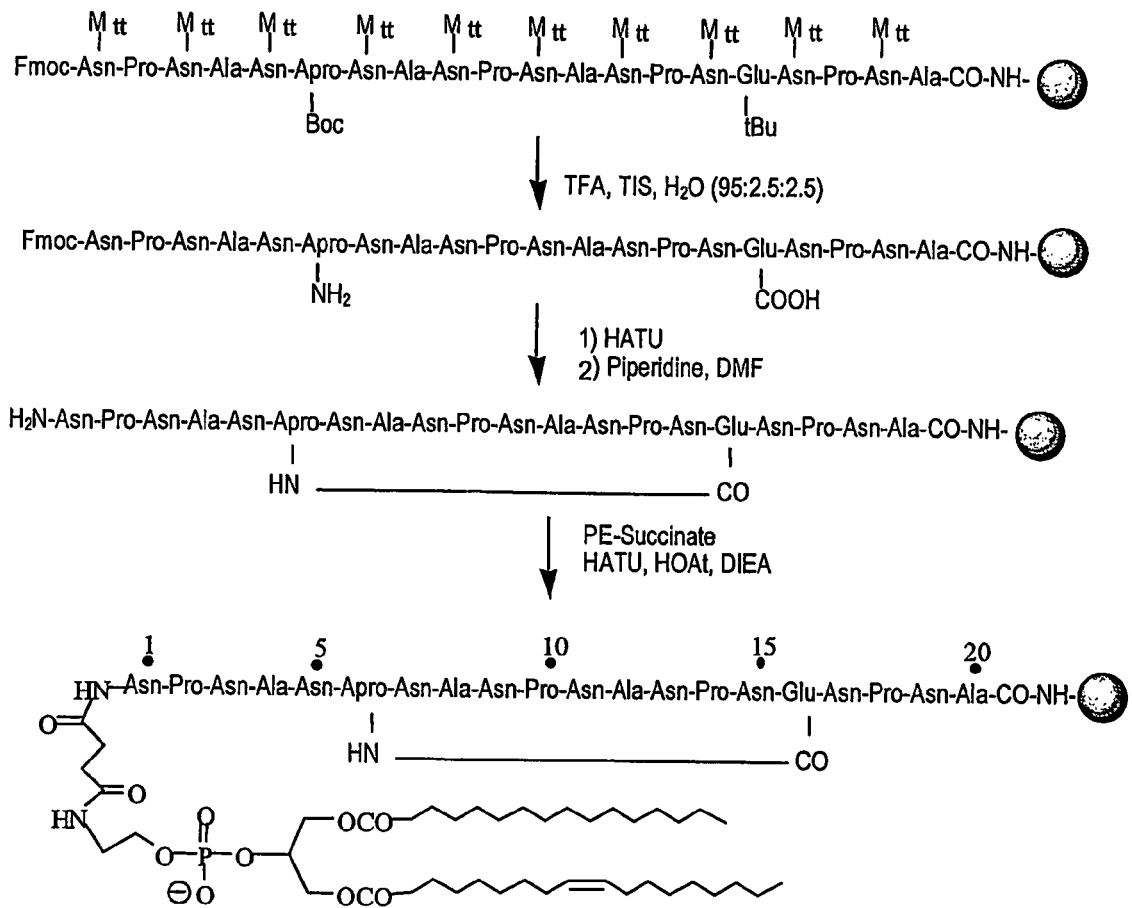
Figure 1:
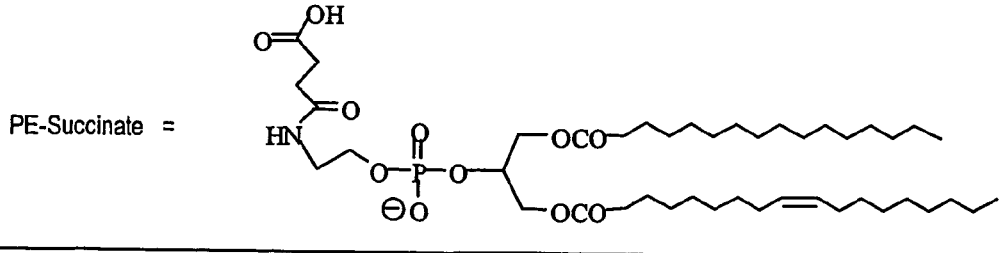

METHOD FOR SYNTHESIZING CONFORMATIONALLY CONSTRAINED PEPTIDES, PEPTIDOMIMETICS AND THE USE THEREOF AS SYNTHETIC VACCINES

The present invention relates to methods for synthesizing conformationally constrained peptides and cyclic peptidomimetics obtainable by these methods which are conformationally constrained due an internal cross-link. This cross-link is formed between the side chain of an amino acid residue or analog and a (2S, 4S)-4-functionalized proline residue. The invention further relates to the use of (2S, 4S)-4-functionalized proline residues as building units in the synthesis of such peptidomimetics and to the use thereof as antigens, alone or in combination with suitable immunopotentiating delivery systems, for example immunopotentiating reconstituted influenza virosomes to elicit an immune response in a mammal. Moreover, the invention also relates to compositions containing the same.

New scientific knowledge and technologies allow to identify and localize essential neutralizing epitopes of microorganisms causing infections and other diseases. These antigen structures can often be mimicked using small linear peptides or polypeptides which are generally designated as peptidomimetics. Such mimetics appear to be promising candidates for vaccination strategies and in the design of novel synthetic vaccines.

However, conformation plays a key role in the ability of peptides to elicit antibody responses against folded proteins. Linear peptides often elicit antibodies that bind well to denatured proteins, but less frequently recognize conformational epitopes in native protein structures. In general, these peptides are more conformationally mobile and therefore unlikely to adopt a stable secondary structure in aqueous solution which corresponds to the three-dimensional epitope on the surface of a protein.

To overcome these limitations, conformational constraints can be incorporated into the primary peptide chain which will reduce the degree of structural flexibility. If the "frozen" conformation of such a peptide imitates the corresponding secondary structure of the target epitope, the peptide antigen can be used to raise antibodies which potentially cross-react with protein structures bearing such epitopes.

There are several approaches known in the prior art to introduce conformational constraints into a linear peptide or polypeptide chain. For example, bridging between two neighbouring amino acids in a peptide leads to a local conformational modification, the flexibility of which is limited in comparison with that of regular peptides. Some possibilities for forming such bridges include incorporation of lactams and piperazinones (for review see Giannis & Kolter, Angew. Chem. Int. Ed., 1993, 32: 1244).

Global restrictions in the conformation of a peptide are possible by limiting the flexibility of the peptide strand through cyclization (Hruby et al., Biochem. J., 268:249, 1990). The common modes of cyclization are the same found in naturally occurring cyclic peptides. These include side chain to side chain cyclization or side chain to end-group cyclization. Another common cyclization is the end-to-end cyclization.

Another conceptual approach to the conformational constraint of peptides was introduced by Gilon, et al., (Biopolymers, 31:745, 1991) who proposed backbone to backbone cyclization of peptides. The theoretical advantages of this strategy include the ability to effect cyclization via the carbons or nitrogens of the peptide backbone without interfering with side chains that may be crucial for interaction with the antibody.

Yet another approach in the design of conformationally constrained peptidomimetics, which is described in U.S. Ser. No. 10/114,918, is to attach a short amino acid sequence of interest to a template, to generate a cyclic constrained peptidomimetic. Such cyclic peptidomimetics are not only structurally stabilized by their templates, and thereby offer three-dimensional conformations that may imitate conformational epitopes on viruses and parasites, but they are also more resistant than linear peptides to proteolytic degradation in serum.

U.S. Ser. No. 10/114,918 further discloses the synthesis of conformationally constrained cross-linked peptidomimetics by preparation of synthetic amino acids for backbone coupling to appropriately positioned amino acids in order to stabilize the supersecondary structure of, mimetics. Cross-linking can be achieved by amide coupling of the primary amino group of an orthogonally protected (2S, 3R)-3-aminoproline residue to a suitably positioned side chain carboxyl group of glutamate. This approach has been followed in the preparation of conformationally constraint tetrapeptide repeats of the CS protein wherein at least one proline has been replaced by 2S, 3R)-3-aminoproline and, in order to introduce a side chain carboxyl group, glutamate has been incorporated as a replacement for alanine.

There are several approaches in the prior art to use modified proline analogs for incorporating conformational constraints into peptides. For example, Zhang et al., J. Med Chem., 1996, 39: 2738-2744, describes synthesis and biological testing of several cyclic analogs of angiotensin II being cyclized between positions 5 and 7 to study the conformational features of molecular recognition of angiotensin II. Cyclization has been achieved by forming amide bonds between 4-amino-trans-proline and side chain carboxyl groups of aspartate and glutamate on one hand and on the other hand, by disulfide bridges between homocysteine residues and 4-mercapto-trans/cis-prolines.

Furthermore, (2S, 3R, 4R)-diaminoproline as a diketopiperazine was incorporated by solid-phase peptide synthesis into a protein loop mimetic. This was shown by NMR analysis to adopt a stable beta-hairpin conformation in DMSO (Pfeifer & Robinson, Chem. Comm., 1998, 1977-1978).

Vaccination is arguably the most successful medical invention and global vaccination programs have yielded impressive results. However, the appearance of novel infectious diseases of global threat, like AIDS and the comeback of infectious diseases that seemed to be mastered by chemotherapy, like tuberculosis and malaria causes a great need to develop new sophisticated vaccines.

In particular, malaria is an increasing health problem throughout the third world. Several hundred million people suffer from the disease and the most acute form, caused by the protozoan parasite *Plasmodium falciparum*, kills over a million children each year in Africa alone.

There is presently no effective vaccine against the parasite, and older established drugs like chloroquine are rapidly loosing their effectiveness due to resistance. On the other hand, ongoing research has provided many new antigens as potential malaria vaccine candidates.

Several antibody targets on the malaria parasite have been identified, one of which is the circumsporozoite (CS) protein present on the surface of early sporozoites (Potocnjak et al., J. Exp. Med., 1980, 151: 1504-1513). The central portion of the CS protein ($M_r$=44 kDa contains 41 tandem repeats of a tetrapeptide, 37 of which are Asn-Ala-Asn-Pro and four of which are Asn-Val-Asp-Pro (Godson et al., Nature, 1983, 305: 29-33; Dame et al., Science, 1984, 225: 593-599).

It was shown that linear tandemly repeated NANP peptides can. elicit antibodies in mice and rabbits that recognize the native CS protein and block sporozoite invasion of hepatocytes (Dame et al., Science, 1984, 225: 593-599; Ballou et al., Science, 1985, 228: 996-999; Young et al., Science, 1985, 228: 958-962; and Zavala et al., Science, 1985, 228: 1436-

1440). These results were a prelude to vaccination studies in humans with synthetic (Asn-Ala-Asn-Pro)$_3$ peptides conjugated to tetanus toxin. However, the immune response was not strong enough for these conjugates to be useful as malaria vaccine (Herrington et al., Nature, 1987, 328: 257). Subsequently, a number of studies were initiated to optimise the immune response to (Asn-Ala-Asn-Pro)$_n$ peptides (Etlinger et al., Eur. J. Immunol., 1991, 21: 1505-1511; Tam et al., J. Exp. Med., 1990, 171: 299-306; Pessi et al., Eur. J. Immunol., 1991, 21: 2273-2276; and deOliviera et al., Vaccine, 1994, 12: 1012-1017).

All of these efforts should be seen in view of the fact that the conformations of the (Asn-Ala-Asn-Pro) repeats in the CS protein were not known and so could not be taken into account in the design process. It seemed most likely that short linear (Asn-Ala-Asn-Pro)$_3$ peptides would be largely unstructured in aqueous solution, and be susceptible to rapid proteolytic degradation in serum. A later study also suggested that a significant part of the immune response against a linear (Asn-Ala-Asn-Pro)$_3$ peptide is directed against the chain termini, which of course are not present in the native CS protein (Etlinger & Trzecjak, Phil. Trans. Roy. Soc. Lond. B, 1993, 340: 69-72). Although the structure of the (Asn-Ala-Asn-Pro)-repeat region in the CS protein is still unknown, modelling suggests that the (Asn-Pro Asn-Ala-Asn)-motif may adopt a helical beta-turn, which is tandemly repeated in the CS protein to generate a novel supersecondary structure. Cyclic peptidomimetics of this (Asn-Pro Asn-Ala-Asn)-motif were synthesized and shown by NMR to adopt helical turns in aqueous solution (Pfeifer et al., Chimia, 2001, 55(4): 334-339).

Using the approach to incorporate conformational constraints by means of internal cross-linking, U.S. Ser. No. 10/114,918 describes the preparation of a conformationally constrained peptidomimetic corresponding to the afore-mentioned tetrapeptide repeat region of the CS protein. In a five-fold repeat, one proline residue has been replaced by (2S, 3R)-3-aminoproline and further, one alanine residue has been replaced by glutamate. Internal cross-linking has then been achieved by amide coupling between the primary amino group of the modified proline unit and the side chain carboxyl group of glutamate.

As outlined above, peptide and protein mimetics are potentially of great value in synthetic vaccine design. The mimetics should function by stimulating the immune system to produce antibodies that recognize the intact parasite. However, the difficulty of presenting in a mimetic the conformational epitopes found on the native antigenic that are required for protective antibody responses are not yet fully overcome.

There is still a need for new routes to incorporate conformational constraints into a linear peptide chain to freeze a specific conformation. Since it is impossible to exactly predict the final conformation of the resulting peptide, it is generally required to create a whole set of constrained peptides of the same primary sequence, which are then analysed for their ability to mimick an epitope of the antigenic protein. For example, such an analysis can be carried out by testing the individual constrained peptides for their cross-reactivity towards known antibodies of said antigenic protein. It is therefore necessary to have a variety of different modes for incorporating a conformational constraint into a precursor peptide at hand.

Surprisingly, it has now been found that conformationally constrained peptides which are cyclized through a 4-substituted proline residue, having a specific stereochemistry, provide for a distinct and unique three-dimensional structure of a given peptide. The conformational constraint is achieved by an internal cross-link between a modified proline residue carrying a functional group at the 4-position and a spatially adjacent side chain functional group of a second residue. The modified proline residue is characterised by a (2S, 4S) stereochemistry.

Cyclic peptidomimetics cyclized via (2S, 4S)-4-substituted proline residues provide for a new class of conformationally constrained peptides which appear to be more stable in aqueous solution and consequently less prone to degradation in serum when, for example, administered as vaccine.

Synthesis of peptidomimetics containing (2S, 4S)-4-substituted proline residue(s) are much easier accessible as for example their 3-substituted counterparts due to a shortened synthesis route comprising less individual steps. Furthermore, starting materials to synthesize the (2S, 4S)-4-substituted proline unit are available in large amounts as they are standard substances which can directly be purchased from several suppliers, for example from Neosystem, 7 rue de Boulogne, 67100 Strasbourg, France.

The incorporation of a (2S, 4S)-4-substituted proline residue instead of, for example a 3-substituted proline unit achieves a conformationally constrained peptide which has a substantially altered three-dimensional peptide structure. It is surprising that this minor change of the chemical structure has such a strong impact on the conformation and immunogenicity of the resulting peptide of the peptide.

Amino acids and amino acid residues described herein may be referred to according to the accepted one or three letter code referenced in text books well known to those of skill in the art, such as Stryer, Biochemistry, 4$^{th}$ Ed., Freeman and Co., New York, 1995 and Creighton, Proteins, 2"d Ed. Freeman and Co. New York, 1993.

As used herein, the terms "peptide" and "polypeptide" are used synonymously and in their broadest sense to refer to a compound of two or more amino acid residues, or amino acid analogs. The amino acid residues may be linked by peptide bonds, or alternatively by other bonds, e.g. ester, ether etc. As used herein, the term "amino acid" or "amino acid residue" refers to either natural and/or unnatural or synthetic amino acids, including both the D or L enantiomeric forms, and amino acid analogs.

The term "epitope" or "B cell epitope" as used herein, designates the structural component of a molecule that is responsible for specific interactions with corresponding antibody (immunoglobulin) molecules elicited by the same or related antigen. More generally, the term refers to a peptide having the same or similar immunoreactive properties, such as specific antibody binding affinity, as the antigenic protein or peptide used to generate the antibody. An epitope that is formed by a specific peptide sequence generally refers to any peptide which is reactive with antibodies against the specific sequence.

The term "antigen" as used herein, means a molecule which is used to induce production of antibodies. The term is alternatively used to denote a molecule which is reactive with a specific antibody.

The term "immunogen" as used herein, describes an entity that induces antibody production in a host animal. In some instances the antigen and the immunogen are the same entity, while in other instances the two entities are different.

The term "immunopotentiating" is used herein to refer to an enhancing effect on immune functions which may occur through stimulation of immune effector cells and may lead to increased resistance to infectious or parasitic agents.

The term "synthetic" as used herein relates to peptides produced by a chemical method as described above, for example.

The term "peptidomimetic" is used herein to denote a peptide or peptide analog that biologically mimics active determinants on parasites, viruses, or other bio-molecules.

The term "conformation" as used herein denotes the various nonsuperimposable three-dimensional arrangements of atoms that are interconvertible without breaking covalent bonds.

In a first embodiment, the present invention relates to a method for synthesizing a conformationally constrained peptide which comprises one or more regions of general formula (I):

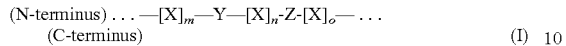

wherein X=an amino acid residue or an amino acid analog and can be the same of different if n>1;
m,o≧0 and n≧1, preferably ≧2;
Y,Z=A or B and Y≠Z, wherein
A=a 4-FgA-proline residue, wherein FgA is a functional group at the 4-position of the proline residue;
B=an amino acid residue or an amino acid analog having a side chain functional group FgB,
wherein the functional groups FgA and FgB are capable of forming an internal link by coupling the functional group FgA at the 4-position of A and the side chain functional group FgB of B;

and comprises the following steps of (a) providing amino acid residues Y and Z having appropriate functional groups FgA and FgB, said functional groups being optionally protected, (b) synthesizing a linear peptide comprising the amino acid residues Y and Z, and (c) optionally deprotecting, if said functional groups are optionally protected, and reacting the functional groups FgA and FgB for converting the linear peptide into the cross-linked form by coupling the functional group FgA at the 4-position of the proline residue (A) and the side chain functional group FgB of B.

Preferably, A is a (2S, 4S)-4-FgA-proline residue, more preferably a (2S, 4S)-4-aminoproline residue. Preferably, B is an amino acid residue or an amino acid analog having a side chain carboxyl group, preferably glutamate or aspartate, wherein an internal cross-link is formed between A and B by amide coupling the amino group at the 4-position of the (2S, 4S)-4-aminoproline residue and the carboxyl group of B.

Preferably, said conformationally constrained peptide is capable of eliciting a pathogen-specific immune response in a mammal.

It is preferred that the linear peptide of step (b) comprises one or more portions of the malaria circumsporozoite (CS) protein of a *Plasmodium* species, preferably *Plasmodium falciparum*. More preferably, this sequence comprises one or more tetrapeptides, which are selected from the group consisting of Asn-Pro-Asn-Ala, Asn-Pro-Asn-Val, Asp-Pro-Asn-Ala and Asp-Pro-Asn-Val.

Preferably, the method for synthesizing conformationally constrained peptides according to the present invention is carried out using solid phase synthesis techniques in the assembling step (c). The linear peptide can be assembled using Fmoc-chemistry. Cleavage from the resin and removal of side-chain protecting groups can proceed in one step and the introduction of the internal cross-link between the (2S, 4S)-4-substituted proline unit, preferably (2S, 4S)-4-aminoproline, and a spatially adjacent side chain functional group can be achieved by cyclization in dimethylformamide (DMF) with a coupling reagent such as O-(7-Azabenzotriazole-1-yl)-N,N,N',N-tetramethyluronium-hexafluorophosphate (HATU).

Optionally, this method further includes the step of attaching the cyclized peptide to a phospholipid moiety (e.g. PE). The phospholipid anchor is preferably attached via a linker, preferably a dicarboxylate linker, more preferably a succinate linker.

In another embodiment, this invention relates to conformationally constrained peptides which are obtainable by the method(s) according to the invention. These peptides comprise one or more regions of general formula (I):

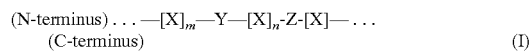

wherein X=an amino acid residue or an amino acid analog and can be the same of different if n>1;
m,o≧0 and n≧1, preferably ≧2;
Y,Z=A or B and Y≠Z, wherein
A=a 4-FgA-proline residue, wherein FgA is a functional group at the 4-position of the proline residue;
B=an amino acid residue or an amino acid analog having a side chain functional group FgB,
wherein the functional groups FgA and FgB are forming an internal link by coupling the functional group FgA at the 4-position of the proline residue and the side chain functional group FgB of B.

Preferably, A is a (2S, 4S)-4-FgA-proline residue, more preferably a (2S, 4S)-4-aminoproline residue.

Preferably, the functional groups FgA and FgB are chosen to form a cyclic ester or cyclic amide bond. Preferably, B is an amino acid residue or an amino acid analog having a side chain carboxyl group, preferably glutamate or aspartate, wherein an internal cross-link is formed between A and B by amide coupling the amino group at the 4-position of the (2S, 4S)-4-aminoproline residue and the carboxyl group of B.

More preferably, the functional group at the 4-position of the modified proline unit is an amino group and cyclization is achieved through amide coupling of said 4-amino of (2S, 4S)-4-aminoproline (Apro) to a side chain carboxyl group FgB of an spatially adjacent residue.

More preferred are peptides wherein the internal cross-link forming residues A and B are separated by more than one amino acid residues or analogs, i.e. n≧2.

Another embodiment of the invention relates to peptides which are conformationally constrained due to an internal cross-link between a (2S, 4S)-4-functionalized proline unit and a suitable side chain functional group of a second residue and which are mimicking the three-dimensional structure of, for example, an epitope on the surface of an antigenic protein. These peptides, designated hereinafter as peptidomimetics, are characterized in that the above-described internal cross-link stabilizes a supersecondary 3D structure of the peptide.

To form this internal cross-link between the modified proline unit and the side chain of another spatially adjacent amino acid residue or analog, said side chain must provide a suitable functional group to allow the formation of a stable chemical bond between both residues. Preferably, the amino acid residue or analog B is selected from the group consisting of glutamate and aspartate and the afore-mentioned internal cross-link is formed through amide coupling with (2S, 4S)-4-aminoproline. More preferably, B is glutamate.

Therefore, the present invention also refers to the use of a 4-Fg-proline, preferably a (2S, 4S)-4-Fg-proline for synthesizing conformationally constrained peptides, wherein Fg is a functional group, selected from amino, hydroxy, sulfhydryl, halogen, sulfonyl, carboxy, thiocarboxy or substituted derivatives thereof, and being preferably selected from amino, hydroxy, halogen, carboxy, or substituted derivatives thereof The invention furthermore refers to such conformationally constrained peptides in which at least one 4-Fg-proline, preferably a (2S, 4S)-4-Fg-proline is incorporated.

The conformationally constrained peptides according to the present invention closely resemble the three-dimensional conformations found on an intact pathogenic protein, thus providing improved epitopes for the generation of pathogen-specific antibodies that efficiently cross-react with pathogens.

In yet another embodiment, the inventive peptide comprises one or more portions of the malaria circumsporozoite (CS) protein of a *Plasmodium* species, preferably of *Plasmodium falciparum*.

Protection of mammals, including man, against infection by the etiologic agent of malaria, *Plasmodium* can be achieved by eliciting an immune response directed against the circumsporozoite (CS) protein. Four species of *Plasmodium* are known to infect man. These are *P. falciparum, P. vivax, P. ovale* and *P. malariae*. The CS protein of *P. falciparum* comprises about 412 amino acids with an approximate molecular weight of 44,000. It comprises 41 tandem repeats of a tetrapeptide. Synthetic peptides of a length of 5-20 residues derived from the repeat region of the CS protein of *P. falciparum* are preferred.

Although, the three-dimensional structure of the tetrapeptide repeat region in the CS protein is still unknown, theoretical studies suggest that it is likely to adopt a stable and repetitious conformation, possibly based on beta-helical turns or similar structures. The present invention provides peptides for the molecular mimicry of the conformational epitopes of the native malaria CS protein which are structurally optimized in order to elicit cross-reactive antibodies with higher efficiency.

structures are close to the preferred conformation of the tetrapeptide-repeat region in the native CS protein. Furthermore, 2D NOESY (nuclear Overhauser enhancement spectroscopy) spectra of conformationally constrained peptidomimetics may be examined for connectivities between the peptide NH groups in the tandemly repeated helical turns. Such connectivities provide evidence for the relatively stable helical turn formation in the context of a supersecondary structure conformation.

In a more preferred embodiment, the invention relates to peptides wherein at least one of said Asn-Pro-Asn-Ala tetrapeptides is replaced by Asn-Pro-Asn-Glu and wherein the glutamate residue of Asn-Pro-Asn-Glu forms an internal cross-link through amide coupling with (2S, 4S)-4-aminoproline.

Preferably, the peptide comprises one or more units of formula (II):

Formula (II):

(N-terminus) ... -Asn-Pro-Asn-Ala-Asn-Apro-(Asn-Ala-Asn-Pro)$_2$-Asn-Glu-Asn-Pro-Asn-Ala- ... (C-terminus)

HN————————CO wherein Apro is (2S, 4S)-4-aminoproline.

It is more preferred that the peptide essentially comprises a five-fold tandem repeat of (Asn-Pro-Asn-Ala) of the CS protein of *P. falciparum*, wherein Pro of the second repeat is replaced by a (2S, 4S)-4-aminoproline unit and alanine of the fourth repeat is replaced by glutamate (formula III, hereinafter denoted as UK39).

Formula (III):

H$_2$N-Asn-Pro-Asn-Ala-Asn-Apro-Asn-Ala-Asn-Pro-Asn-Ala-Asn-Pro-Asn-Glu-Asn-Pro-Asn-Ala-COOH

HN————————CO

In a preferred embodiment of the invention, the peptide comprises one or more tetrapeptides selected from the group consisting of Asn-Pro-Asn-Ala, Asn-Pro-Asn-Val, Asp-Pro-Asn-Ala and Asp-Pro-Asn-Val. More preferably, these peptides comprise 3 to 10, and most preferably 4 to 6 of such tetrapeptide units.

The present invention relates to peptidomimetics for the, molecular mimicry of the conformational epitopes of the CS protein of *Plasmodium* species, preferably *P. falciparum*. More preferably, the conformationally constrained peptide comprises (Asn-Pro-Asn-Ala)$_n$ wherein n is 2, 3, 4 or 5.

Models of these conformationally constrained peptidomimetics may be assessed for the stability and adoption of supersecondary structure in molecular dynamics (MD) simulations in solvent. Adoption of a supersecondary structure by these model peptidomimetics may be evidence that their wherein Apro is (2S, 4S)-4-aminoproline.

Through amide coupling, an internal cross-link is formed which stabilizes a structure mimicking the native conformation of CS-protein tandem repeat epitopes.

As described in more detail in the following example, modeling studies concerning the peptidomimetic UK39 (formula V) have revealed a unique and distinct conformation compared to the isomeric mimetic BP66 which merely differs to UK39 in that the cyclization has been achieved through (2S, 3R)-3-aminoproline. Due to the easily accessible (2S, 4S)-4-aminoproline, UK39 (in contrast to BP66) can be obtained by a short and standardized synthesis route. Since UK39 requires less individual synthesis steps and the starting material are cataloged standard substances and are therefore available in large quantities, high amounts of UK39 can easily be obtained in higher amounts if compared to the corresponding synthesis of BP66.

Furthermore, UK39 is less prone to be degraded in aqueous solution than its isomeric counterpart BP66. This is apparently due to a gain of stability of the conformation.

Moreover, UK39 shows an excellent antigenicity and parasite clearance in vivo. If compared with BP66, it is a better mimetic. With regard to cross reactivity to antibodies which were raised against *P. falciparum,* more antibodies bind to UK39 than to BP66.

The skilled artisan will appreciate that the afore-mentioned beneficial features are not limited to amide bond cyclizations. That is to say, UK39 derivatives wherein the internal cross-link is formed by a disulfide bridge or by an ester bond, i.e. wherein the modified proline unit is (2S, 4S)-4-mercaptoproline or (2S, 4S)-4-hydroxyproline, respectively, and wherein in the first case alanine is replaced by cysteine instead of glutamate are also encompassed by the present invention. The specific conformation behind the afore-mentioned beneficial features is essentially determined by the stereochemistry and the position of the cross-linking functional group at the modified proline ring.

The skilled artisan will appreciate that the afore-mentioned antigenic polypeptide molecules may be administered with one or more adjuvants in order to enhance the immunological response. For example, depending on the host species, adjuvants which may be used include, but are not limited to: mineral salts or mineral gels such as aluminum hydroxide, aluminum phosphate, and calcium phosphate; surface active substances such as lysolecithin, pluronic polyols, polyanions, peptides, oil emulsions, keyhole limpet hemocyanins, and dinitrophenol; immunostimulatory molecules, such as cytokines, saponins, muramyl dipeptides and tripeptide derivatives, CpG dinucleotides, CpG oligonucleotides, monophosphoryl Lipid A, and polyphosphazenes; particulate and microparticulate adjuvant, such as emulsions, liposomes, virosomes, cochleates; or an immune stimulating complex mucosal adjuvants, Freund's (complete and incomplete, and potentially useful human adjuvants such as BCG (bacille Calmette-Guerin) and corynebacterium parvum.)

In another embodiment, the peptides according to the invention are coupled to a phospholipid. Preferably, the N-terminus which may have one or more double bonds and may be same or different.

Formula (IV):

The peptides according to the invention can be used in synthetic vaccine design. Peptidomimetics function by stimulating the immune system to produce antibodies that recognize the intact parasite. Preferably, such mimetics are presented to the immune system in a way that leads to a more efficient antibody production. For example, cyclic peptidomimetics can be presented on immunopotentiating reconstituted influenza virosomes (IRIVs) or liposomes, a form of antigen delivery that is practised already in human clinical use.

The attachment of a phospholipid anchor to the N-terminus of peptidomimetics functioning as antigen allows to combine the peptide with immunopotentiating delivery systems. According to a further aspect of the invention, peptides are thus preferred which are combined with an immunopotentiating delivery system. Preferred immunopotentiating delivery systems are selected from the group consisting of liposomes, multiple-antigen peptides and immunopotentiating reconstituted virosomes.

For example, immunopotentiating reconstituted influenza virosomes (IRIV) as human compatible immunopotentiating delivery agents are capable of presenting the conformationally constrained peptidomimetics in multiple copies to the immune system and therefore, further improves the generation of efficient pathogen cross-reactive antibody responses. IRIVs are spherical, unilamellar vesicles, prepared from a mixture of phospholipids and influenza virus surface glycoproteins. The hemgglutinin membrane glycoprotein of influenza virus plays a key role in the mode of action of IRIVs. This major antigen of influenza is a fusion-inducing component, which facilitates antigen delivery to immunocompetent cells.

In addition, peptides according to the invention (T cell epitopes) can be encapsulated into virosomes in order to be protected from enzymatic degradation by the body fluids and will be presented to the immune system via the MHC I class pathway.

of these peptides is coupled via a linker, preferably a dicarboxylate linker, more preferably a succinate linker to a fatty acid derivative of phosphaditylethanolamine, preferably 1-palmitoyl-3-oleoyl-phosphatidylethanolamine (PE, formula IV). Said fatty acid derivative is preferably a mono- to di-ester of glycerol with one or two $C_{10}$ to $C_{30}$ fatty acids Particularly preferred is a peptide of five (Asn-Pro-Asn-Ala) tandem repeats that is internally cross-linked as described above and which further comprises a PE moiety at the N-terminus which provides for the attachment to an immunopotentiating reconstituted influenza virosome (formula V).

Formula (V):

```
        1              5              10             15             20
HN-Asn-Pro-Asn-Ala-Asn-Apro-Asn-Ala-Asn-Pro-Asn-Ala-Asn-Pro-Asn-Glu-Asn-Pro-Asn-Ala-CO ⎯⎯ NH⎯●
```

For in vivo experiments peptides according to the invention can be combined with adjuvants in order to enhance the immunological response. For example, depending on the host species, adjuvants which may be used include, but are not limited to: mineral salts or mineral gels such as aluminum hydroxide, aluminum phosphate, and calcium phosphate; surface active substances such as lysolecithin, pluronic polyols, polyanions, peptides, oil emulsions, keyhole limpet hemocyanins, and dinitrophenol; immunostimulatory molecules, such as cytokines, saponins, muramyl dipeptides and tripeptide derivatives, CpG dinucleotides, CpG oligonucleotides, monophosphoryl Lipid A, and polyphosphazenes; particulate and microparticulate adjuvant, such as emulsions, liposomes, virosomes, cochleates; or an immune stimulating complex mucosal adjuvants, Freund's (complete and incomplete, and potentially useful human adjuvants such as BCG (bacille Calmette-Guerin) and corynebacterium parvum.) However, it is noted that strong adjuvants, e.g. Freund's adjuvants can cause severe undesirable side effects that they are not accepted by regulatory authorities for human use.

Yet another embodiment concerns the use of (2S, 4S)-4-substituted proline for synthesizing conformationally constrained peptides. Preferably, this covalently modified proline is used in one of the above described method for synthesizing conformationally constrained peptides which have been cyclized through coupling of said modified proline unit, preferably (2S, 4S)-4-aminoproline, and a second residue of the peptide chain. In this method, (2S, 4S)-4-aminoproline is incorporated during the assembling step (b).

The cross-linked peptidomimetic can be prepared by solid phase synthesis methods well-known in the art. The linear peptide can be assembled using Fmoc-chemistry. Cleavage from the resin and removal of side-chain protecting groups can proceed in one step and the key backbone coupling of the modified proline residue and glutamate can be achieved by cyclization in DMF with a coupling reagent such as HATU.

In a further embodiment, the invention relates to the use of the inventive peptides for the manufacture of a vaccine for the treatment of malaria. Preferably, conformationally constrained peptidomimetics of the central (Asn-Pro-Asn-Ala) repeat region of the CS protein of the malaria parasite P. falciparum can be used to mimick the surface structure of CS protein and thereby elicit a humoral immune response. Antibodies raised against such a mimetic are capable to cross-react with the native CS protein on P. falciparum sporozoites. Therefore, peptidomimetics according to the invention can be widely used in the design of molecularly defined combined synthetic vaccines, including those targeted against multiple antigens and development stages of P. falciparum, and against other infectious agents.

In a further embodiment, the invention concerns a method for producing antibodies in a host against Plasmodium species, preferably against Plasmodium falciparum comprising the step of administering an above-described peptide to said host.

Another embodiment of the present invention relates to an in vitro method for detecting Plasmodium species in a sample comprising the steps (a) contacting said sample with an antibody according to the invention under conditions such that binding to CS protein epitopes occurs if CS protein is present; and (b) detecting the presence of said antibody bound to an CS protein epitope.

In detail, the method comprises incubating a test sample with one or more antibodies of the present invention and assaying whether the antibody binds to the test sample. The presence of CS protein may indicate malaria disease.

Conditions for incubating an antibody with a test sample vary. Incubation conditions depend on the format employed in the assay, the detection methods employed and the type and nature of the antibody used in the art. Examples of such assays can be found in Tijssen, "Practice and theory of enzyme immunoassays: Laboratory Techniques in Biochemistry and Molecular Biology," Elsevier Science Publishers, NL (1985).

Yet another embodiment of the present invention relates to a kit for detecting the presence of Plasmodium species in a sample, wherein said kit comprises: (i) a first container means containing an antibody according to the invention, and (ii) second container means containing a conjugate comprising a binding partner of the antibody and a label. In another preferred embodiment, the kit further comprises one or more other containers comprising one or more of the following: wash reagents and reagents capable of detecting the presence of bound antibodies.

Examples of detection reagents include, but are not limited to, labeled secondary antibodies, or in the alternative, if the primary antibody is labeled, the chromophoric, enzymatic, or antibody binding reagents which are capable of reacting with the labeled antibody.

Figure 2:
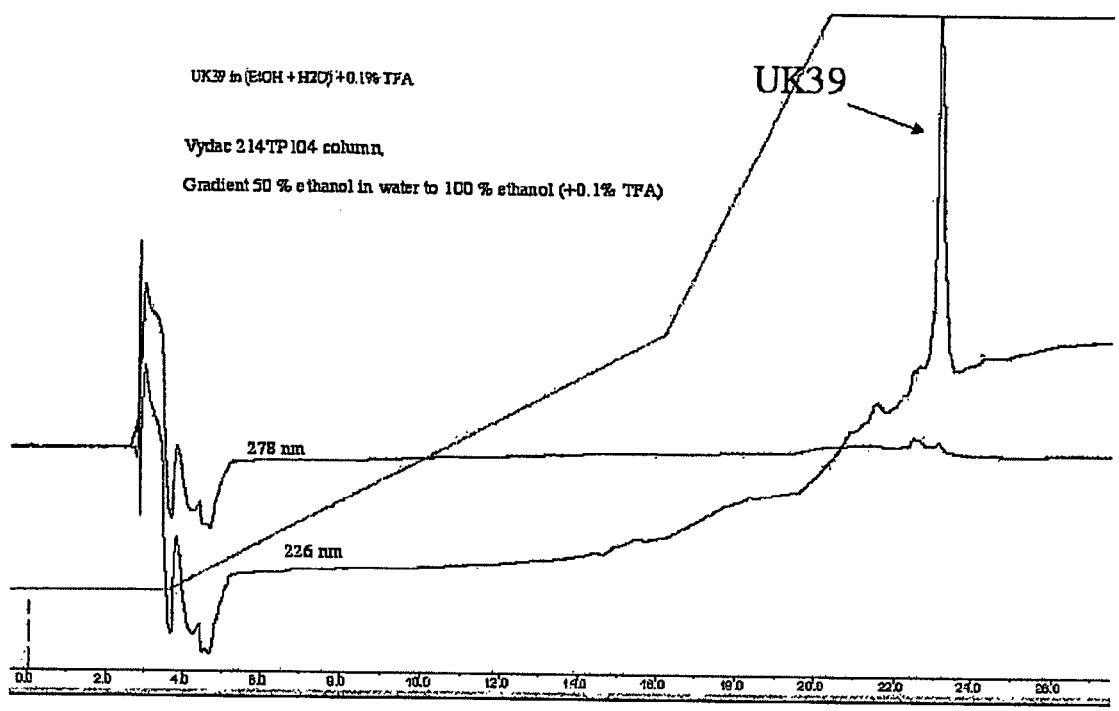

Having now generally described the present invention, the same may be more readily understood by reference to the following example in connecting with the accompanying FIGS. 1-2.

FIG. 1 schematically illustrates the route of synthesis to the conformationally constrained peptidomimetic Asn-Pro-Asn-Ala-Asn-(Apro-Asn-Ala-Asn-Pro-Asn-Ala-Asn-Pro-Asn-Glu)$_{cyclo}$-Asn-Pro-Asn-Ala attached to a PE moiety.

FIG. 2 shows the grade of purification of the inventive peptidomimetic according to formula (IV) in an HPLC chromatogram. After completing the synthesis, the solvent was removed and, the resulting residue purified using a C4 reverse phase HPLC column (Vydac 214 TP 1010, 25 cm×10 mm) using a gradient starting with 50% ethanol in water to 100% ethanol (+0.1% TFA) over 15 minutes. UK39 appears as a broad peak at about 90% ethanol. m/z 1427 $(M+2H)^{2+}$.

Figure 3:
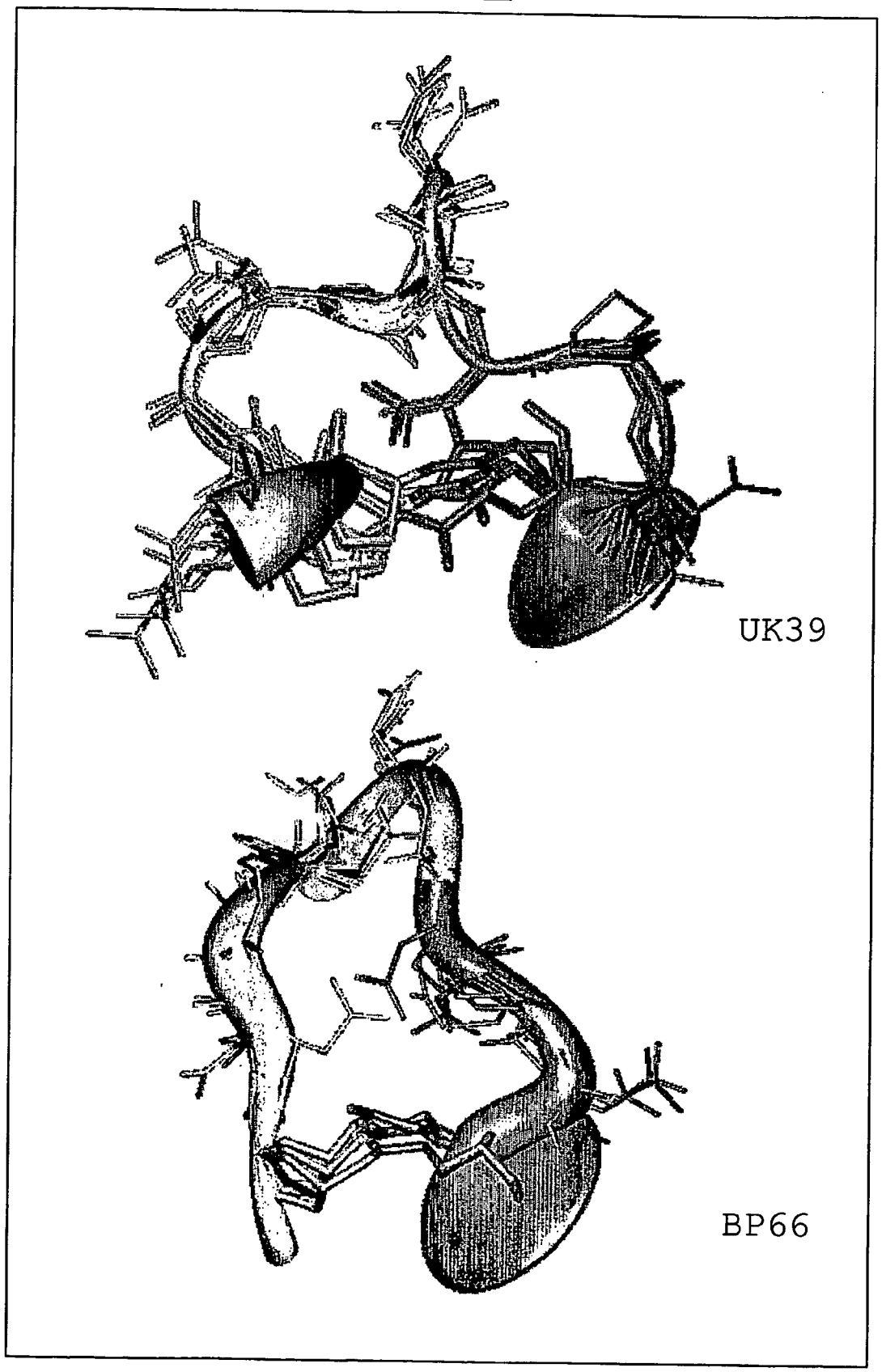

FIG. 3 shows a comparison of average NMR structures in aqueous solution of the prior art peptide BP66 and the peptide UK39 according to the present invention. BP66 only differs to UK39 in that the modified proline unit (2S, 4S)-4-aminoproline has been replaced by the (2S, 3R)-3-aminoproline isomer. Due to the change of the position of the cross-link from the 3-to the 4-position, the conformation of the entire macrocyclic portion of the peptide has been changed. The figure shows average NMR structures deduced in water by NMR and dynamic simulated annealing (SA). The figure was prepared using MOLMOL (Konradi R. et al., J. Mol. Graph. 1996, 14, 51-55).

It should be understood that the following example is for illustrative purposes only and should not be construed as limiting this invention in any way to the specific embodiment recited therein.

Unless otherwise specified, general chemical and peptide synthesis procedures, such as those set forth in Voet, Biochemistry, Wiley, 1990; Stryer; Peptide Chemistry. A Practical Textbook, 2nd ed., Miklos Bodanszky, Springer-Verlag, Berlin, 1993; Principles of 15 Peptide Synthesis, 2nd ed., Miklos Bodanszky, Springer-Verlag, Berlin, 1993; Chemical Approaches to the Synthesis of Peptides and Proteins, P. Lloyd-Williams, F. Albericio, E. Giralt, CRC Press, Boca Raton, 1997; Bioorganic Chemistry: Peptides and Proteins, S. M. Hecht, Ed., Oxford Press, Oxford, 1998, are used.

EXAMPLES

Synthesis and Purification of the Inventive Peptidomimetic According to Formula (V)

The following demonstrates the synthesis of the conformationally constrained peptidomimetic Asn-Pro-Asn-Ala-Asn-(Apro-Asn-Ala-Asn-Pro-Asn-Ala-Asn-Pro-Asn-Glu)$_{cyclo}$-Asn-Pro-Asn-Ala attached to a PE moiety. The synthesis of the linear peptide precursor was performed on Rink Amide MBHA resin (0.73 mM/g) (Novabiochem) on an Applied Biosystems ABI433A peptide synthesizer. The peptide was synthesized on a 0.25 mmol scale using 4 eq of each Fmoc-protected amino acid each activated with HBTU/HOBt (4 eq.). The amino acids used were: Fmoc-Asn(Mtt)-OH, Fmoc-Pro-OH, Fmoc-Ala-OH, Fmoc-Glu(tBu)-OH and Fmoc-(4S, 2S)-4-aminoproline(Boc)-OH.

The cleavage of the linear peptide from the resin was carried out using TFA containing 2.5% TIS and 2.5% water over 3 h at room temp. After removal of most of the TFA in vacuo, the peptide was precipitated using diisopropyl ether, washed with iPr$_2$O, and dried in vacuo for 1 h. The product can be analyzed by reverse phase HPLC on a C18 column using a gradient of MeCN/H$_2$O (+0.1% TFA; 5–>95% MeCN ; $t_R$=10 min). m/z: 2294 $(M+H)^+$.

For cyclization, the crude linear peptide from above was stirred overnight at room temp. together with 4 eq HATU, 4 eq HOAt in DMF and 1% v/v DIEA (2 mg/ml peptide). The solvent was removed and the peptide dissolved in 20% piperidine/DMF and stirred for 15 min. at room temp. to remove the Fmoc group. The solvent was evaporated and peptide was precipitated using diisopropyl ether and dried in vacuo. The product can be analyzed by reverse phase HPLC on a C18 column using a gradient of MeCN/H$_2$O (+0.1% TFA; 5–>95% MeCN ; $t_R$=11 min). m/z: 2276 $(M+H)^+$.

The foregoing product (40 mg) in DMF (5 ml) with 4 eq each of HATU/HOAt was treated with a solution of PE-CO—(CH$_2$)$_2$—COOH (PE-succinate; 4 eq.) in DCM (5 ml) together with 1% of DIEA and stirred overnight at room temp. The solvent was removed and the resulting residue purified using a C4 reverse phase HPLC column (Vydac 214 TP 1010, 25 cm×10 mm) using a gradient starting with 50% ethanol in water to 100% ethanol (+0.1% TFA) over 15 minutes. UK39 appears as a broad peak at about 90% ethanol. m/z 1427 $(M+2H)^{2+}$ (see below).

Cross-Reactivity to Antibodies Raised Against the CS Protein of *P. Falciparum*

The following demonstrates the cross-reactivity of both UK39 and the isomeric form BP66 to antibodies raised against the CS protein of *P. falciparum*. BP66 merely differs to UK39 in that the modified proline unit (2S, 4S)-4-aminoproline (formula VI) of UK39 has been replaced by the (2S, 3R)-3-aminoproline isomer.

Tab. 1 shows that more monoclonal antibodies raised against the CS protein bind to UK39 than to BP66. Peptidomimetic UK39 comprising (2S, 4S)-4-aminoproline thus provide for an improved mimicking of the tandem repeat region of the CS protein The benefits in immunological reactivity arise from the use of (2S, 4S)-4-aminoproline rather than the earlier (2S, 3R)-3-aminoproline. So the improvement arises by moving the site of cross-linking from the 3- to the 4-position of the proline ring. The immunological response generated by the novel mimetic is stronger and different. This difference is seen in the fact that a monoclonal antibody could be isolated from the immunization with the mimetic containing (2S, 4S)-4-aminoproline that binds the parasite but does not bind the mimetic containing 3-aminoproline. This indicates that the new molecule mimics parts of the parasite surface protein that are not represented at all in the earlier mimetic containing (2S, 3R)-3-aminoproline (the antibody binds the parasite and the mimetic with (2S, 4S)-4-aminoproline but not the mimetic with 2S, 3R)-3-aminoproline). This can be easily rationalized, since by changing the position of the cross-link from the 3-position to the 4-position the inventors inevitably changed the conformation (shape) of the macrocyclic portion of the molecule. This is a crucial part for recognition by antibodies. Molecular modelling studies with both mimetics supports the notion that changing the position of the cross-link also changes the conformation of the backbone. The change in conformation may be small. But even small changes in conformation may lead to changes in the way the mimetic is recognized by antibodies, and hence change the ability of the molecule to mimic epitopes on the surface of the parasite (Table 1).

TABLE 1

Immunological cross-reactivity of monoclonal antibodies raised against *P. falciparum* sporozoites with the closely related mimotopes UK39 and BP66.

| Mab | BP 66 | UK 39 |
|---|---|---|
| Sp4-5F2 | + | + |
| Sp4-2H1 | + | + |
| Sp3-E6 | + | + |
| Sp3-C6 | + | + |
| Sp3-E9 | + | + |
| Sp4-4B6 | + | + |
| Sp4-7C2 | + | + |
| Sp4-7E4 | + | + |
| Sp4-7H1 | − | + |
| Sp4-4D7 | + | + |
| Sp3-B4-C12 | + | + |
| Sp4-1B4 | − | + |

Modelling of the Conformation of the Conformationally Constrained Peptidomimetics UK39 and BP66

To determine which conformation the constrained peptide antigen will adopt in aqueous solution, the peptidomimetic can be studied by NMR and MD methods in aqueous solution in analogy to previous studies (Bisang, C. et al., J. Am. Chem. Soc. 1998, 120, 7439-7449). Average solution structures for the conformationally constrained peptidomimetics are calculated using NOE-derived distance restraints by dynamic simulated annealing (SA) and moleculare dynamics (MD.) simulations, using methods described earlier (Bisang, C. et al., J. Am. Chem. Soc. 1998, 120, 7439-7449)

Modeling studies concerning UK39 and BP66 show that cyclization through the (2S, 4S)-4-aminoproline residue stabilizes the conformation of UK39. Moreover, modeling reveals that BP66 adopts a different structure than UK39. Therefore, it can be concluded that the change of the cyclization from position 3 to 4 together with the specific stereochemistry of the primary amino group at the modified proline residue creates a new conformation in the NPNA motifs.

Preparation of Mimetic-Loaded Virosomes

For the preparation of PE-mimetic-IRIV, a solution of 4 mg purified Influenza A/Singapore hemagglutinin is centrifuged for 30 min at 100,000 g and the pellet is dissolved in 1.33 ml. of PBS containing 100 mM OEG (PBS-OEG). 32 mg phosphatidylcholine (Lipoid, Ludwigshafen, Germany), 6 mg phosphatidylethanolamine and the PE-mimetics are dissolved in a total volume of 2.66 ml PBS-OEG. The phospholipids and the hemagglutinin solution are mixed and sonicated for 1 min. This solution is then centrifuged for 1 hour at 100,000 g and the supernatant is sterile filtered (0.22 μm). Virosomes are then formed by detergent removal using BioRad SM BioBeads (BioRad, Glattbrugg, Switzerland).

Immunogenicity Studies for the UK39-Peptidomimetic-IRIV

Antibody responses elicited by IRIVs loaded with the conformationally constrained peptidomimetic UK39 are studied in BALB/c mice. Preimmunization is achieved with the influenza vaccine Inflexal Berna TM (Berna-Products, Bern, Switzerland). Immunization is achieved with several doses of IRIV-peptidomimetic.

BALB/c mice are preimmunized intramuscularly with commercial whole virus influenza vaccine (0.1 ml; Inflexal Berna, Berna Products, Bern, Switzerland) on day 21. Starting on day 0, they received at three-weekly intervals three doses of conformationally constrained UK39 peptidomimetic linked to IRIV intramuscularly at doses of 50 μg of mimetic. Blood is collected two weeks after the third immunization and analyzed by ELISA and IFA.

Enzyme-Linked Immunosorbent Assays (ELISA)

ELISA microtiter plates (Immunolon 413, Dynatech, Embrach, Switzerland) are coated at 4° C. overnight with 50 ml of a 5 mg/ml solution of peptidomimetic constructs in PBS, pH 7.2. Wells are then blocked with 5% milk powder in PBS for 1 h at 37° C. followed by three washings with PBS containing 0.05% Tween-20. Plates are then incubated with twofold serial dilutions of mouse serum or hybridoma cell supernatants in PBS containing 0.05% Tween-20 and 0.5% milk powder for 2 h at 37° C. After washing, the plates are incubated with alkaline phosphatase-conjugated goat anti mouse IgG (g-chain specific) antibodies (Sigma, St. Louis, Mo.) for 1 h at 37° C. and then washed. Phosphatase substrate (1 mg/ml p-nitrophenyl phosphate, Sigma) in buffer (0.14% $Na_2CO_3$, 0.3% $NaHCO_3$, 0.02% $MgCl_2$, pH 9.6) is added and incubated at room temperature. The optical density (OD) of the reaction product is recorded after appropriate time at 405 nm using a microplate reader (Titertek Multiscan MCC/340, Labsystems, Finland). Titration curves are registered and analyzed using GENESIS LITE 2.16 software (Life Sciences Ltd., Basingstoke, UK). Effective dose 20% values (ED20%) are calculated for each curve and the corresponding titers are set as endpoint titers.

Immunofluorescence Assays

Immunofluorescence assays are performed to assess cross-reactivity of the antibodies obtained. Air-dried unfixed *P. falciparum* salivary gland sporozoites (strain NF54) attached to microscope glass slides are incubated in a moist chamber for 20 min at 37° C. with serum diluted in PBS. The slides are then washed five times with PBS containing 0.1% bovine serum albumin (PBS-BSA) and dried. FITC-labelled goat anti-mouse IgG (Fab-specific) antibodies (Sigma), optimally diluted in PBS containing 0.1 g/l Evans43lue (Merck, Germany), are added. After incubation for 20 min at 37° C. the slides are again washed five times with PBS-BSA, dried, mounted with glycerol, and covered with a cover slide. A Leitz Dialux 20 microscope using 12.5/18 ocular and a 40x/1.30 oil fluorescence 160/0.17 objective is used to detect fluorescence staining at 495 nm excitation and 525 nm emission wavelengths.

The invention claimed is:

1. A peptide comprising one or more units of formula (II):

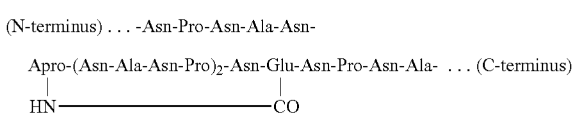

wherein Apro is (2S, 4S)-4-aminoproline.

2. The peptide of claim 1 having the formula (III):

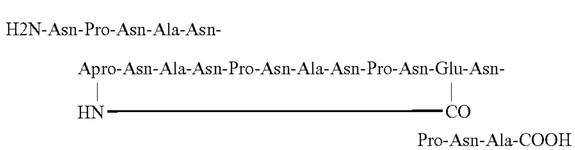

3. The peptide of claim 1, wherein said peptide is coupled to a phospholipid.

4. The peptide of claim 3, wherein the N-terminus of said peptide is coupled via a linker to a phosphatidylethanolamine.

5. The peptide of claim 4, wherein said linker is a dicarboxylate linker.

6. The peptide of claim 5, wherein said dicarboxylate linker is a succinate linker.

7. The peptide of claim 4, wherein the phosphatidylethanolamine is 1-palmityl-3-oleoylphosphatidylethanolamine (PE).

8. The peptide of claim 1, wherein said peptide is combined with an immunopotentiating delivery system, which is selected from the group consisting of liposomes, multiple-antigen peptides and immunopotentiating reconstituted virosomes.

9. The peptide of claim 2, further comprising a PE moiety at the N-terminus attached to an immunopotentiating reconstituted virosome.

10. A composition comprising one or more peptides of claim 1.

11. The composition of claim 10 further comprising one or more pharmaceutically acceptable adjuvants.

* * * * *

SEQUENCE LISTING

```
<160> NUMBER OF SEQ ID NOS: 10

<210> SEQ ID NO 1
<211> LENGTH: 4
<212> TYPE: PRT
<213> ORGANISM: Artificial
<220> FEATURE:
<223> OTHER INFORMATION: Tandem repeat sequence of the central portion
      of CS-protein

<400> SEQUENCE: 1

Asn Ala Asn Pro
1

<210> SEQ ID NO 2
<211> LENGTH: 4
<212> TYPE: PRT
<213> ORGANISM: Artificial
<220> FEATURE:
```

```
<223> OTHER INFORMATION: Tandem repeat sequence of the central portion
      of CS-protein

<400> SEQUENCE: 2

Asn Val Asp Pro
1

<210> SEQ ID NO 3
<211> LENGTH: 12
<212> TYPE: PRT
<213> ORGANISM: Artificial
<220> FEATURE:
<223> OTHER INFORMATION: Tandem repeat sequence of the central portion
      of CS-protein

<400> SEQUENCE: 3

Asn Ala Asn Pro Asn Ala Asn Pro Asn Ala Asn Pro
1               5                   10

<210> SEQ ID NO 4
<211> LENGTH: 5
<212> TYPE: PRT
<213> ORGANISM: Artificial
<220> FEATURE:
<223> OTHER INFORMATION: Tandem repeat sequence of the central portion
      of CS-protein

<400> SEQUENCE: 4

Asn Pro Asn Ala Asn
1               5

<210> SEQ ID NO 5
<211> LENGTH: 4
<212> TYPE: PRT
<213> ORGANISM: Artificial
<220> FEATURE:
<223> OTHER INFORMATION: Portion of the malaria circumsporozoite (CS)
      protein of a Plasmodium species

<400> SEQUENCE: 5

Asn Pro Asn Ala
1

<210> SEQ ID NO 6
<211> LENGTH: 4
<212> TYPE: PRT
<213> ORGANISM: Artificial
<220> FEATURE:
<223> OTHER INFORMATION: Portion of the malaria circumsporozoite (CS)
      protein of a Plasmodium species

<400> SEQUENCE: 6

Asn Pro Asn Val
1

<210> SEQ ID NO 7
<211> LENGTH: 4
<212> TYPE: PRT
<213> ORGANISM: Artificial
<220> FEATURE:
<223> OTHER INFORMATION: Portion of the malaria circumsporozoite (CS)
      protein of a Plasmodium species

<400> SEQUENCE: 7

Asp Pro Asn Ala
1
```

-continued

<210> SEQ ID NO 8
<211> LENGTH: 4
<212> TYPE: PRT
<213> ORGANISM: Artificial
<220> FEATURE:
<223> OTHER INFORMATION: Portion of the malaria circumsporozoite (CS) protein of a Plasmodium species

<400> SEQUENCE: 8

Asp Pro Asn Val
1

<210> SEQ ID NO 9
<211> LENGTH: 4
<212> TYPE: PRT
<213> ORGANISM: Artificial
<220> FEATURE:
<223> OTHER INFORMATION: Modified protein sequence of a tandem repeat sequence of the central portion of CS-protein

<400> SEQUENCE: 9

Asn Pro Asn Glu
1

<210> SEQ ID NO 10
<211> LENGTH: 20
<212> TYPE: PRT
<213> ORGANISM: Artificial
<220> FEATURE:
<223> OTHER INFORMATION: conformational constrained peptidomimetic
<220> FEATURE:
<221> NAME/KEY: misc_feature
<222> LOCATION: (6)..(6)
<223> OTHER INFORMATION: Amide coupling of (2S,4S)-4-aminoproline in pos. 6 with glutamate residue in pos. 16

<400> SEQUENCE: 10

Asn Pro Asn Ala Asn Xaa Asn Ala Asn Pro Asn Ala Asn Pro Asn Glu
1 5 10 15

Asn Pro Asn Ala
20